United States Patent [19]

Jannard

[11] Patent Number: 4,730,915
[45] Date of Patent: Mar. 15, 1988

[54] DETACHABLE COMPONENT SUNGLASSES

[75] Inventor: James H. Jannard, Laguna Niguel, Calif.

[73] Assignee: Oakley, Inc., Irvine, Calif.

[21] Appl. No.: 787,242

[22] Filed: Oct. 15, 1985

Related U.S. Application Data

[63] Continuation-in-part of Ser. No. 690,642, Jan. 11, 1985, Pat. No. 4,674,851.

[51] Int. Cl.⁴ .............................................. G02C 9/00
[52] U.S. Cl. ..................................... 351/47; 351/44; 351/57
[58] Field of Search .................... 351/44, 47, 41, 57; 2/426, 429

[56] References Cited

U.S. PATENT DOCUMENTS

| D. 145,288 | 7/1946 | DiCicco . |
| D. 163,869 | 7/1951 | Hinman . |
| D. 176,316 | 12/1955 | Fleming . |
| D. 187,394 | 3/1960 | Moeller . |
| D. 199,150 | 9/1964 | Carmichael . |
| D. 210,048 | 1/1968 | Imperatrice . |
| D. 268,683 | 4/1983 | Tenny . |
| D. 285,020 | 8/1986 | Schmidthaler . |
| 2,444,498 | 7/1948 | Cochran . |
| 2,472,731 | 6/1949 | Splaine . |
| 2,482,664 | 9/1949 | Gagnon . |
| 2,582,345 | 1/1952 | Moeller . |
| 3,531,189 | 9/1970 | Petito . |
| 3,689,136 | 9/1972 | Atamian . |
| 3,708,222 | 1/1973 | Lindblom ............................. 351/62 |
| 3,756,704 | 9/1973 | Marks .................................. 351/60 |
| 4,515,448 | 5/1985 | Tackles . |
| 4,564,272 | 1/1986 | Rinnooy Kan ..................... 351/153 |

FOREIGN PATENT DOCUMENTS

| 673815 | 4/1929 | France . |
| 790755 | 5/1935 | France . |
| 2472764 | 12/1979 | France . |

Primary Examiner—John K. Corbin
Assistant Examiner—P. M. Dzierzynski
Attorney, Agent, or Firm—Knobbe, Martens, Olson & Bear

[57] ABSTRACT

Sunglasses have a unitary transparent pane extending in a curved plane and over the wearer's nose bridge. The sunglasses frame and nose-piece construction permits their ease of removal and replacement, as well as pane replacement; and provision is made for stem pull-away; frame padding; and elastomeric pads to engage the sides of the wearer's nose.

14 Claims, 16 Drawing Figures

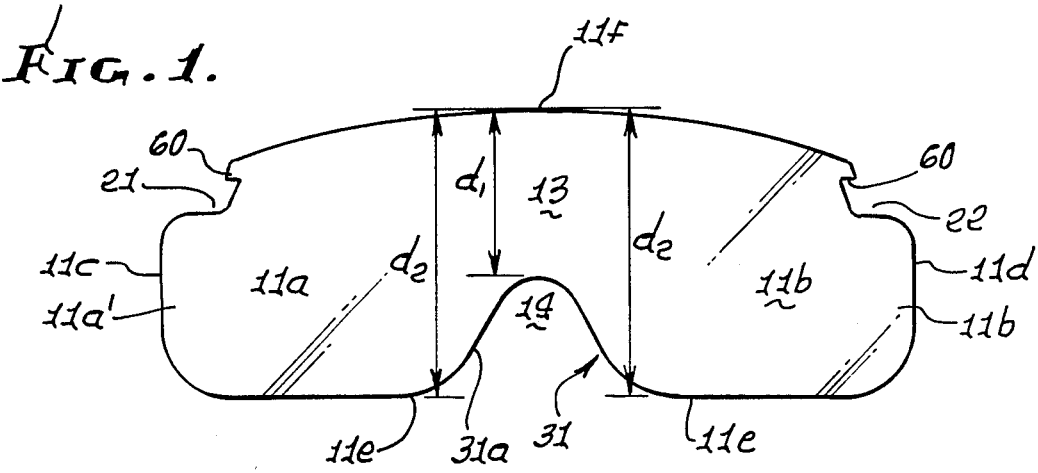
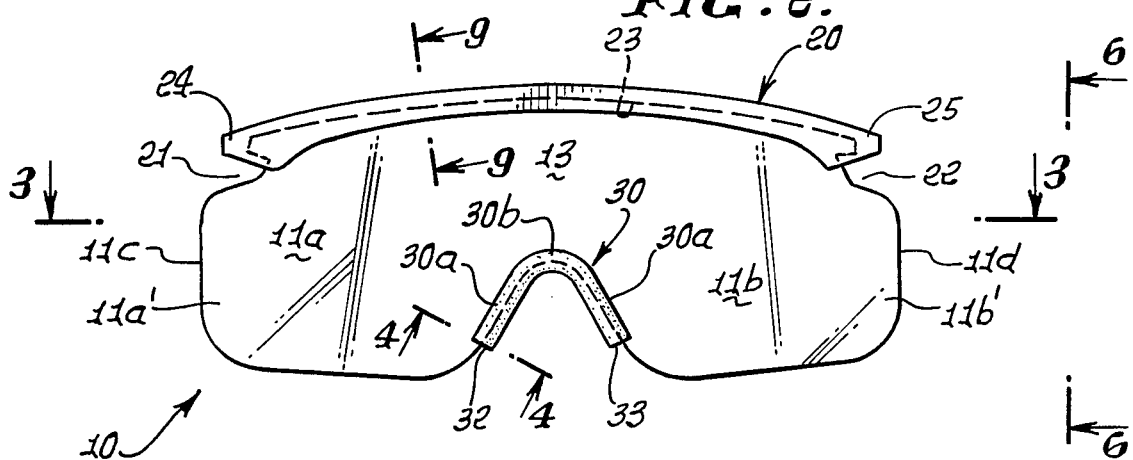
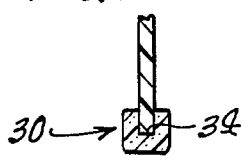
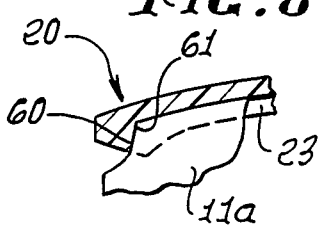
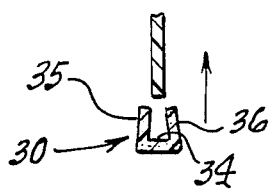
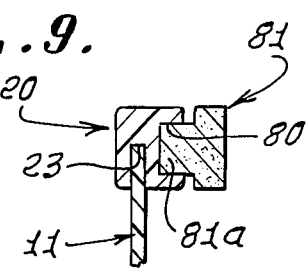

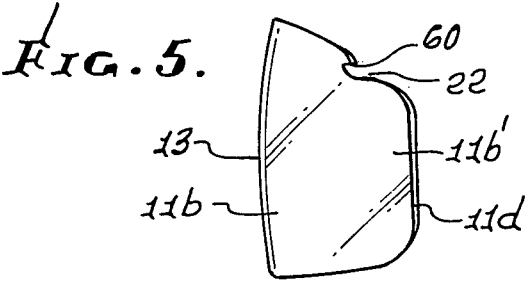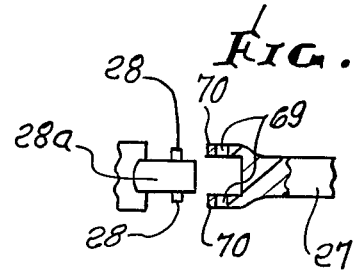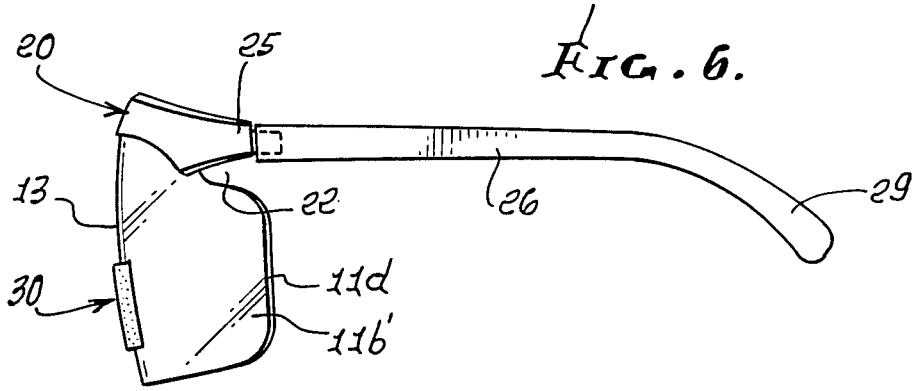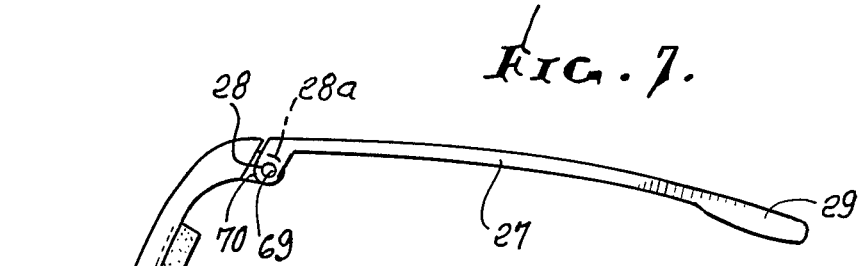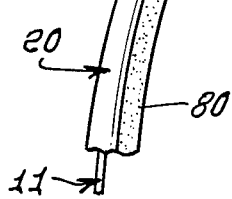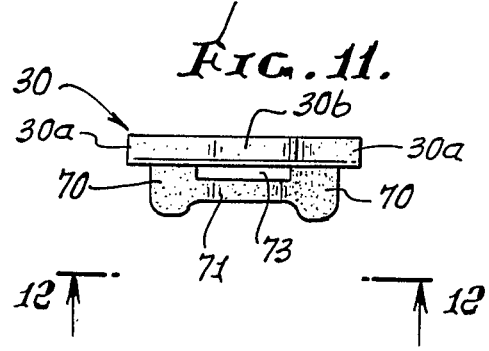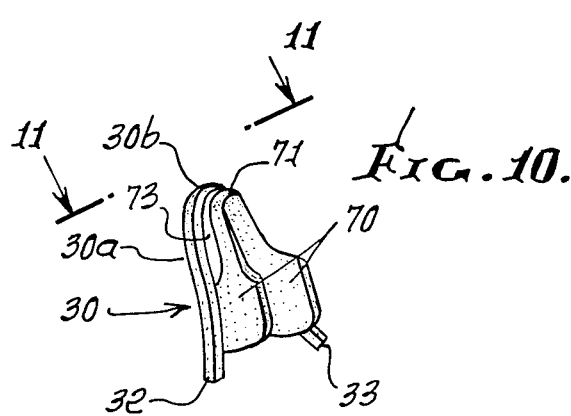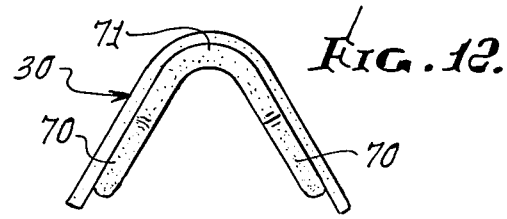

DETACHABLE COMPONENT SUNGLASSES

BACKGROUND OF THE INVENTION

This application is a continuation-in-part of U.S. Ser. No. 690,642, filed Jan. 11, 1985, which is issued on June 23, 1987 as U.S. Pat. No. 4,674,851.

This invention relates generally to eyewear, and more particularly to construction of sunglasses.

There is a need for sunglasses which more completely intercept sunlight at the top, bottom and sides of the glasses; also there is need for sunglasses which permit ease of pane or lens removal and replacement, and also replacement or substitution of different nose pieces and frames, to better fit the wearer. There is also need for simplicity of frame, nose piece and lens assembly construction, together with means to reduce air turbulence and moisture on the lens, near the eyes of the wearer, and for stem pull-away.

SUMMARY OF THE INVENTION

It is a major object of the invention to provide improved sunglasses which meet the above needs, and which also incorporate other unusual advantages in construction, modes of adjustment, and results, as will appear. Basically, the improved eyeglasses comprise a unitary transparent lens or pane located to extend in the paths of the wearer's fields of vision, frontwardly and sidewardly; and the lens extends in a plane which may be frusto-conical when attached to the frame, partially wrapping around the sides of the head to intercept peripheral vision. The result is better interception of sunlight, top to bottom and side-to-side, the lens matching closely the wearer's facial contour. No distortion is introduced because of absence of local suddenly increased curvature or break in shape.

As will be seen, the protective eyeglasses or sunglasses basically comprise:

(a) a unitary transparent pane located to extend in a curved plane in the path of the wearer's field of vision, both frontally and sidewardly, that curved plane being frusto-conical, the pane having an upwardly humped lower edge bounding a space to receive the wearer's nose, (b) a top frame extending along and bounding upper edge extent of the pane, and arms or stems attached to the top frame at opposite ends thereof, with "pull-free" construction, and adapted to extend rearwardly to the wearer's ears, (c) and a nose piece bounding the unitary pane upwardly humped lower edge, and having nose engaging elastomeric pads, (d) at least one of said top frame and nose piece having removable attachment to the unitary pane.

As will be seen, both the top frame and nose piece typically have removable attachments to the unitary pane, such attachments being independent to permit selective removal and replacement of the nose piece and top frame, as well as the pane itself; in this regard, the wearer can thereby easily assemble these components from a group of same, of different sizes, to best fit his facial and head contours. Preferably, the curved pane is cylindrical in the as-molded condition, but deformed slightly by its cooperation with a slot in the top frame to have frusto-conical curvature, and it consists of synthetic resin.

Another object of the invention is to provide a replaceable nose piece including nose engaging pads that consist of a relatively soft elastomeric material having a coefficient of sliding friction that increases when said material is wetted, such material typically being hydrophilic. Foam padding may be carried by the top frame to engage the wearer's forehead.

It is a further object to provide sunglasses having a unitary plastic pane free of frame structure along frame edges extending downwardly from locations proximate the attachments of the stems the top frame, and then inwardly toward the nose piece terminals, whereby the top frame is removable relatively upwardly off the unitary pane, and the nose piece is removable relatively downwardly from the unitary pane. As will be seen, the unitary pane may have tang means to interfit the frame.

These and other objects and advantages of the invention, as well as the details of an illustrative embodiment, will be more fully understood from the following specification an drawings in which:

DRAWING DESCRIPTION

FIG. 1 is a front view of a unitary pane, in flattened condition;

FIG. 2 is a frontal view of sunglasses incorporating the invention;

FIG. 4 is an enlarged section on lines 4—4 of FIG. 2; and FIG. 4a is like FIG. 4, prior to assembly of the nose piece to the pane;

FIG. 5 is a side view of the curved pane, in as-molded condition;

FIG. 6 is a side view of the assembled sunglasses, on lines 6—6 of FIG. 2;

FIG. 6a is an inner side view of the ear stem detached from the top frame;

FIG. 7 is a top plan view showing frame and stem hinge structure, and padding;

FIG. 8 is an enlarged fragmentary section showing tang interfit of the unitary pane and top frame;

FIG. 9 is an enlarged section taken on lines 9—9 of FIG. 2, to show frame slots for both the pane and padding;

FIG. 10 is a perspective view of a nose piece with attached elastomeric pads to engage the sides of the wearer's nose;

FIG. 11 is top plan view on lines 11—11 of FIG. 10;

FIG. 12 is a front view on lines 12—12 of FIG. 11;

DETAILED DESCRIPTION

The protective eyeglasses, as for example sunglasses shown at 10 in FIG. 2, include transparent panes or lenses 11a and 11b located to extend in the direct path of the wearer's left and right eye fields of vision. Those panes merge as at bridge 13 directly above the wearer's nose, a generally triangular nose opening being formed at 14. Thus, a unitary or single pane or lens 11 is provided, and may be easily replaced, as for example by panes of lesser or greater darkness, size, or different coloring, etc., as desired by the wearer.

Figure 3:
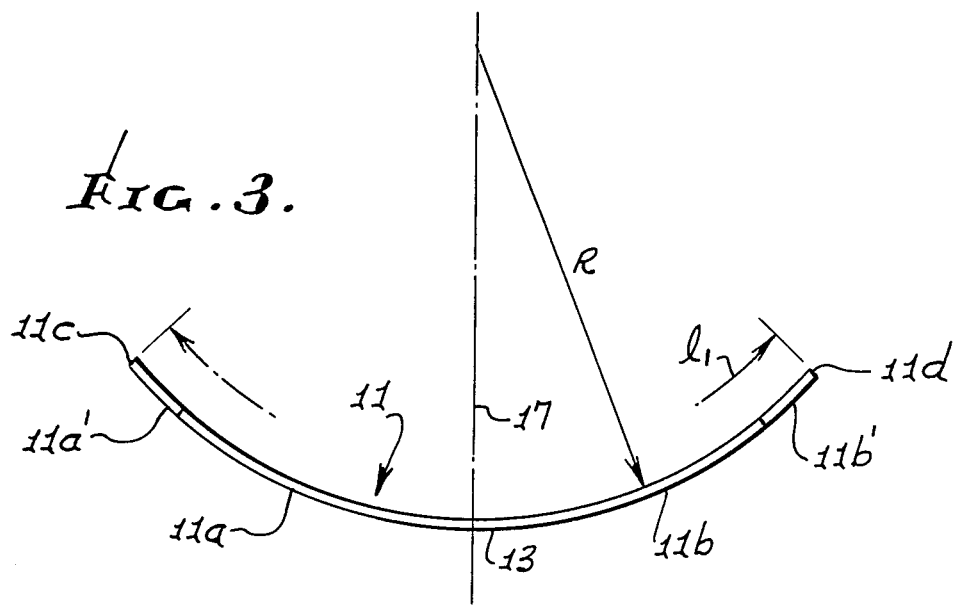
FIG. 3 is a section through the cylindrically normal pane of FIG. 2, on lines 3—3 of FIG. 2.

It is a feature of the invention that the unitary pane extends in a plane which is substantially and preferably precisely cylindrical in as-molded condition. FIG. 3 shows the cylindrical curvature of the single pane, and between opposite end wings 11a' and 11b'. FIG. 1 shows the pane in flattened condition, i.e. pressed into the flat plane of the paper. The panes 11a and 11b and bridge 13 are formed to have cylindrical conformation, which becomes frusto-conical when the pane is attached to top frame 20, such that their curvatures conform very well to the natural curvature of the wearer's face, i.e. his cheek bones and forehead as well as side face configuration. Note that panes 11a and 11b and wings 11a' and 11b' wrap backwardly or rearwardly to extend in the paths of the wearer's sideward fields of vision, without such abruptly changing curvature as would distort the light passing through the side wrapping portions of the panes. The curved planes of panes 11a and 11b are symmetrically located at opposite sides of a plane 17 bisecting the bridge 13, and contained by the axis of the cylinder defined by the panes. For best results, the radius R of curvature of the panes is in the range 3.25 to 5.00 inches, and optimally within the range 3.50 and 4.00 inches.

Also, the pane 11 has a vertical dimension $d_1$ immediately above the nose bridge, $d_1$ being between ¾ inch and 1¼ inches; the pane has generally rearwardly extending lateral terminals 11c and 11d and a length dimension $l_1$ between said terminals, $l_1$ between 5½ and 7 inches, that length dimension measured along the cylindrical curvature of the pane; and the pane has two lowermost terminals 11e, and width dimensions $d_2$ between 2 and 2¾ inches, as measured between those lowermost terminals 11e and the pane uppermost top edge 11f.

Figure 13:
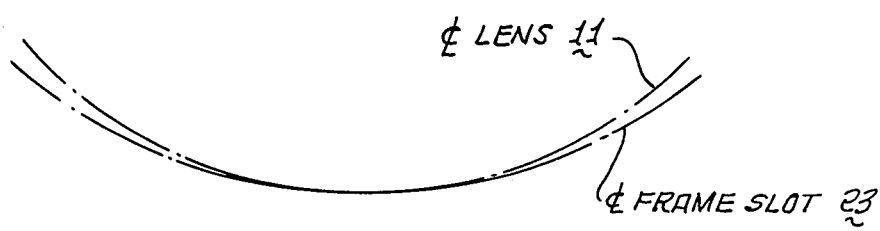
FIG. 13 is a diagram to show mismatch between interfits of the pane and top frame.
Figure 14:
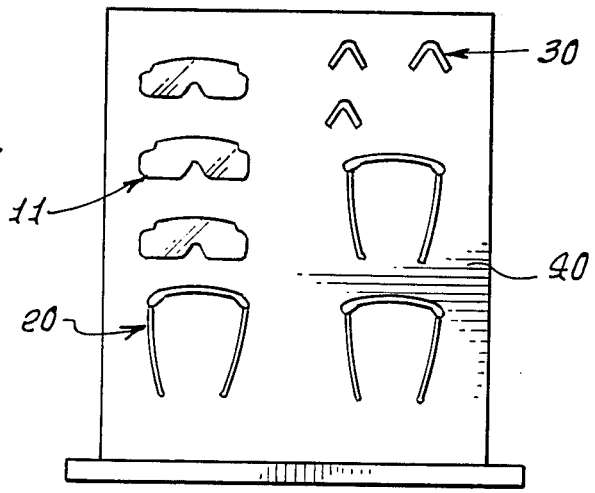
FIG. 14 is a display.

Also provided is a top frame 20 extending along and bounding upper edge extent of the lens or pane 11, as between the notched areas 21 and 22 formed immediately above the wings 11a' and 11b'. The frame may advantageously consist of relatively rigid, molded plastic material, which may be transparent. The top frame is shown as having removable attachment to the top edge extent of the lens or pane, and for this purpose a slot 23 is formed upwardly therein from the bottom of the frame 20, with curvature generally matching that of the lens, to tightly, yet removably receive the lens upper edge extent. For this purpose, the curvature of the slot 23 may be slightly different than the cylindrical, as-molded curvature of the lens, to provide a mismatch, to grip the pane, which then resiliently coacts with the frame to slightly deform the pane to frusto-conical shape. See FIG. 13. Note that the lens upper edge 11f is shown to have slight upward convexity, in FIG. 1, as well as cylindrical curvature, as in FIG. 3. Tang means such as one or more tangs 60 integral with the pane and projecting over notched areas 21 and 22 rearwardly fit in corresponding shallow recesses 61 in the frame, at opposite ends of the slot 23, to help retain the pane in position. See FIG. 8.

The top frame has enlarged end terminals at 24 and 25, that extend in notched areas 21 and 22, and have hinged attachment to two stems or arms 26 and 27 adapted to extend rearwardly to the wearer's ears. See for example the trunnions 28 or tongue 28a integral with top frame 20, and the bearings or openings 69 in flanges 70 integral with the stem, in FIG. 6a. These elements are of molded plastic construction and designed to forcibly interfit, and to allow forcible "pull-away", as during impact, for the safety of the wearer. Stems 27 hook at 29 over the wearer's ears, and may also consist of molded plastic material.

A nose piece 30 bounds the pane upwardly humped lower edge 31, and has terminals 32 and 33 which are laterally spaced apart to be located along the edges 31a of the pane. The nose piece has upwardly extending sections 30a which taper toward one another, in matching relation to pane edges 31a. An upwardly convex section 30b interconnects the sections 30a. The nose piece has a slot 34 formed therein to extend along the wave-shaped length of the nose piece for removable interfit with the pane upwardly humped lower edge, as seen in FIGS. 2 and 4. FIG. 4a shows the nose piece as channel shaped in cross section, with flanges 35 and 36 that taper toward one another, to be spread apart upon reception of the pane, as seen in FIG. 4, providing a removable grip or retention of these elements. The nose piece typically consists of a relatively soft elastomeric material having a coefficient of sliding friction that increases when the material is wetted. Such a material is hydrophilic, and tends to retain the nose piece in position on the wearer's upper nose area as the wearer perspires, or encounters moisture as during skiing. Also, the material is soft, for comfort. One such material is KROTON G, a product of Shell Oil Company. FIGS. 10-12 show the provision of elastomeric pads 70 connected to the nose piece, and adapted to flex and closely fit the opposite sides of the wearer's nose. A V-shaped elastomeric connector 71 joins the pads to reinforce them and yieldably resist pad flexing. Connector 71 parallels the nose piece at 30b, and they define a ventilation slot 73 therebetween to pass air to the rear side of the pane 11 bridge section 13, to resist fogging.

The nose piece 30 and attached pads 70 may be removed, relatively downwardly, and replaced with a selected substitute, having different size, shape or color, to meet the needs of the wearer; also the top frame may be easily removed upwardly from the pane, and replaced with a different size or color frame; or, the pane itself may be replaced with a substitute having different sun blocking shading or composition, color, etc. Thus, the wearer or user may assemble his sunglasses from a large number of different components, as provided on a rack or other display, to result in an assembled sunglasses truly best fitted and best suited, component wise, in every respect to the requirements of the wearer. One such rack is shown at 40 in FIG. 10, with a number of different panes 11, frames 20 and nose pieces 30, having different size, color, etc., characteristics, but interfittable as described above, to provide a custom sunglasses, easily selected, compared, and assembled, by the wearer or dealer.

The notches or notched areas 21 and 22 that extend downwardly proximate the attachments of the hinged connections of the arms to the top frame also open sidewardly. It is found such upper notches draw discharge moisture collecting on rearward surfaces of pane, and below the top frame (which projects rearwardly from the top of the pane). Such discharge is believed due to an aspirating effect of air directed laterally toward the notches at the front of the pane, during forward movement of the wearer (as for example a skier). Also, air turbulence at the reaside of the pane is reduced due to presence of the notches. Accordingly, the wearer's eyes are further protected from air turbulence and moisture, and during skiing, wind surfing, etc.

The frame 20 also has a second slot 80 sunk in its rearward side (see FIG. 9) to receive a tongue portion 81a of a foam pad strip 81. Padding 81 is adapted to engage the wearer's forehead, for comfort, whereby the sunglasses are yieldably supported on the wearer's nose by flexing elastomeric pads 70, and by engagement of pad 80 with the wearer's forehead, as during force application to the sunglasses toward the wearer's face.

I claim:

1. Sunglasses, comprising, in combination:
   (a) a unitary transparent pane located to extend in a curved plane in the path of the wearer's field of vision, both frontally and sidewardly, said curved plane being everywhere substantially cylindrical, the pane having an upwardly humped lower edge bounding a space to receive the wearer's nose,
   (b) a top frame extending along and bounding elongated upper edge extent of the pane, and stems attached to the top frame at opposite ends thereof and adapted to extend rearwardly to the wearer's ears,
   (c) and the top frame having an elongated slot formed to extend upwardly in the frame from the lower side of the frame, along frame length, to removably vertically receive and closely fit the pane upper edge,
   (d) the pane being notched downwardly at two locations respectively proximate the upper opposite ends of the pane, the notches opening sidewardly above opposite end extents of the pane, the top frame having end portions overhanging said notches, and spaced above notch lower edges, said upper edges terminating at said notches,
   (e) the pane including projections overhanging portions of the the notches to interlock within end portions of said slot in the top frame.

2. Sunglasses, comprising, in combination,
   (a) a unitary transparent pane located to extend in a curved plane in the path of the wearer's field of vision, both frontally and sidewardly, said curved pane being everywhere substantially cylindrical, the pane having an upwardly humped lower edge bounding a space to receive the wearer's nose,
   (b) a top frame extending along and bounding elongated upper edge extent of the pane, and stems attached to the top frame at opposite ends thereof and adapted to extend rearwardly to the wearer's ears,
   (c) a nose piece having a slot therein and extending therealong to removably receive and closely fit the pane upwardly humped lower edge,
   (d) and the top frame having an elongated slot formed to extend upwardly in the frame from the lower side of the frame, along frame length, to removably vertically receive and closely fit the pane upper edge,
   (e) the top frame and nose piece independently attached to the pane via the slots in the top frame and nose piece to permit selective removal and repalcement of the top frame and nose piece,
   (f) the pane being notched downwardly proximate the attachments of the stems to the top frame, the notches opening sidewardly above opposite end extends of the pane to draw and discharge moisture collecting on rearward surfaces of the pane during forward movement of the wearer, the top frame overhanging said notches, and spaced above notch lower edges,
   (g) the pane including projections overhanging portions of the notches to interlock within end portions of said elongated slots.

3. Sunglasses as defined in claim 2 wherein the lens sheet has cylindrical curvature, in as-molded condition, prior to assembly to said upper frame.

4. Sunglasses as defined in claim 2 wherein each stem has pivotal attachment to an end portion of the frame, said attachment defined by snap interfit members on the stem and frame to releasably retain the stem to the frame and to allow forcible relative pull-away of the stem from the frame as during accidental impact.

5. Sunglasses as defined in claim 4 wherein said members have tongue and groove configuration.

6. Sunglasses as defined in claim 4 wherein said members include upper and lower trunnions on one of the frame and stem, and trunnion receiving bearings on the other of said frame and stem, the trunnions and bearings having sideward interference fit, allowing forcible pull-away, as defined.

7. Sunglasses as defined in claim 2 wherein the upper frame also has a second slot therein, and a protective pad attached to the frame via said second slot.

8. Sunglasses as defined in claim 7 wherein said pad consists of plastic foam material partially received in said slot.

9. Sunglasses as defined in claim 7 wherein said second slot is at the rear side of the frame adapted to face the wearer's forehead, and said lens receiving slot is at the lower side of the frame.

10. Sunglasses as defined in claim 2 including flexible, elastomeric pads carried by the lens sheet to project away from the sheet at locations to flexibly engage the opposite sides of the wearer's nose.

11. Sunglasses as defined in claim 10 including an inverted V-shaped lower frame attached to inverted V-shape edge extents of the lens sheet, said elastomeric pads attached to said inverted V-shaped lower frame.

12. Sunglasses as defined in claim 11 wherein said lower frame consists of soft elastomeric material.

13. Sunglasses as defined in claim 11 including an inverted V-shaped connector joining said pads and spaced from the lens sheet.

14. Sunglasses as defined in claim 13 wherein said connector and said lower frame define a ventilation slot therebetween to pass ventilation air to the rear side of a nose bridge portion of the lens sheet integral with left and right sheet portions adapted to extend frontwardly of the wearer's eyes, respectively.

* * * * *